United States Patent [19]
Delvecchio et al.

[11] Patent Number: 6,010,848
[45] Date of Patent: Jan. 4, 2000

[54] SCREENING METHODS USING AN ATPASE PROTEIN FROM HEPATITIS C VIRUS

[75] Inventors: Alfred M. Delvecchio, West Chester; Weidong Zhong, Royersford, both of Pa.

[73] Assignee: Smithkline Beecham Corporation, Philadelphia, Pa.

[21] Appl. No.: 09/100,557

[22] Filed: Jun. 19, 1998

Related U.S. Application Data

[60] Provisional application No. 60/051,582, Jul. 2, 1997.

[51] Int. Cl.$^7$ ........................................................ C12Q 1/70
[52] U.S. Cl. ................................................... 435/5; 435/21
[58] Field of Search ............................................ 435/5, 24

[56] References Cited

FOREIGN PATENT DOCUMENTS 0 318 216 B1  12/1993  European Pat. Off. .

OTHER PUBLICATIONS

Neddermann, et al., "The Nonstructural Proteins of the Hepatitis C Virus: Structure and Functions," *Biol. Chem.* 378:469–476, (1997).
Database Caplux on STN, AN 1996: 628463. Takeshita, et al., Aug. 13, 1996. Jpn. Kikai Tokkyo Koho 13 11.

*Primary Examiner*—Donna C. Wortman
*Assistant Examiner*—Brenda G. Brumback
*Attorney, Agent, or Firm*—William T Han; William T King; Charles M Kinzig

[57] ABSTRACT

Disclosed are screening methods to identify molecules which activate or inhibit the activity of an ATPase protein of the Flaviviridae family, particularly NS4B protein of Hepatitis C Virus (HCV). These inhibitors and activators of HCV NS4B protein potentially can be used as antiviral compounds and as therapeutic agents for the treatment of viruses linked to the Flaviviridae family, particularly HCV, flaviviruses such as yellow fever virus, Dengue virus types 1–4, and pestiviruses such as bovine viral diarrhea virus and classic swine fever, among others.

2 Claims, No Drawings

SCREENING METHODS USING AN ATPASE PROTEIN FROM HEPATITIS C VIRUS

CROSS-REFERENCE TO RELATED APPLICATION

This application claims benefit to the earlier provisional U.S. application, Ser. No. 60/051,582, filed on Jul. 2, 1997, the contents of which are incorporated herein by reference in their entirety.

FIELD OF THE INVENTION

This invention relates to the verification of a previously undefined enzymatic activity of an ATPase protein of the Flaviviridae family, particularly hepatitis C virus (HCV) and the NS4B protein. Furthermore, this invention provides screening methods to identify molecules which activate or inhibit the newly discovered activity of this protein.

BACKGROUND OF THE INVENTION

First identified by molecular cloning in 1989 (Choo, et al., *Science* 244: 359–362 (1989)), hepatitis C virus (HCV) is now widely accepted as the most common causative agent of post-transfusion non A, non-B hepatitis (NANBH) (Kuo, et al., *Proc. Natl. Acad. Sci. USA* 87: 2057–2061 (1989)). Infection with HCV is a major cause of human liver disease throughout the world with seroprevalence in the general population ranging from 0.3 to 2.2% (van der Poel, et al., In Reesink, H. W., ed. *HEPATITIS C VIRUS*, Amsterdam:Karger; p. 137–163 (1994)) to as high as ~10–20% in Egypt (Hibbs, et al., *J. Infect. Dis.* 168:789–790 (1993)). Although the virus is most commonly transmitted via blood, the mode of transmission remains unknown for a large portion of infected individuals (Alter, et al., *Infect. Agents Dis.* 2: 155–166 (1993)). Over 50% of infections by HCV progress to acute hepatitis associated with viremia and generally elevated serum alanine aminotranferase (ALT) levels (Alter, H. J., *CURRENT PROSPECTIVE IN HEPATOLOGY*, New York: Plenum p. 83–97 (1989)). Over half of the acute cases progress to a chronic infection with roughly 20% developing cirrhosis (Alter, H. J., *CURRENT PROSPECTIVE IN HEPATOLOGY*, New York: Plenum p. 83–97 (1989)). Chronic infection by HCV has also been linked epidemiologically to the development of hepatocellular carcinoma (HCC), especially in cirrhotic patients (Blum, et al., *Hepatology*. 19: 251–258 (1994)).

Since its initial identification, many isolates of HCV have been sequenced, displaying much genetic diversity and leading to the subclassification of this virus into multiple genotypes (Bukh, et al., *Proc. Natl. Acad. Sci. USA* 90: 8234–8238 (1993); Bukh, et al., *Proc. Natl. Acad. Sci. USA* 91: 8239–8243 (1994); Dusheiko, et al., *Hepatology* 19:13–18 (1994)). Due to its genome structure and sequence homology, this virus was assigned as a new genus in the Flaviviridae family, along with the other two genera, flaviviruses (such as yellow fever virus and Dengue virus types 1–4) and pestiviruses (such as bovine viral diarrhea virus) (Choo, et al., *Science* 244: 359–362 (1989); Miller, et al., *Proc. Natl. Acad. Sci. USA* 87: 2057–2061 (1990)). Like the other members of the Flaviviridae family, HCV is an enveloped virus containing a single-stranded RNA molecule of positive polarity. The HCV genome is approximately 9.6 kilobases (kb) with a long, highly conserved, noncapped 5' nontranslated region (NTR) of approximately 340 bases which functions as an internal ribosome entry site (IRES) (Wang, et al., *Curr. Topics Microbiol. Immunol.* 203: 99–115 (1995)). This element is followed by a region which encodes a single long open reading frame (ORF) encoding a polypeptide of ~3000 amino acids comprising both the structural and nonstructural viral proteins. This large polypeptide is subsequently processed into the individual structural and non-structural proteins by a combination of host and virally-encoded proteinases (reviewed in Rice, B. N. Fields, D. M. Knipe, and P. M. Howley (eds.), *VIROLOGY*, 2d ed., p. 931–960, Raven Press, New York (1996)).

Although a robust culture system for propagating HCV has not yet been reported, the putative functions of the viral gene products were initially predicted by their homology to the viral proteins found in other members of the Flaviviridae family, whose functions were known. Many of these predictions were later demonstrated experimentally for the individual HCV proteins using recombinantly expressed proteins (reviewed in Rice, B. N. Fields, D. M. Knipe, and P. M. Howley (eds.), *VIROLOGY*, 2d ed., p. 931–960, Raven Press, New York (1996)). However, the function of HCV NS4B protein, like that of the NS4B in the other members of the Flaviviridae family, is still unknown.

Inhibition of ATPase proteins of the Flaviviridae family, particularly HCV NS4B protein, is potentially of benefit in controlling, reducing and alleviating the diseases caused by infection with these organisms. There remains a need for treatment, in this field, for compounds which are capable of inhibiting or activating these proteins, in particular HCV NS4B protein.

SUMMARY OF INVENTION

One aspect of the present invention is identification of a previously undefined activity of a protein of the Flaviviridae family, specifically the HCV NS4B protein. It has now been found that this HCV NS4B protein possesses ATPase activity.

Another aspect of this invention provides for a method of identifying a compound that alters the activity of the HCV NS4B protein, which method comprises:

(a) contacting an isolated HCV NS4B protein, or an extract containing NS4B protein, said extract having activity which is only ATPase activity derived from NS4B protein, with a candidate compound; and (b) determining whether the activity of the HCV NS4B protein is altered by said candidate compound. The activity being altered by the compound is ATPase activity.

Yet another aspect of this invention is to the use of the identified agonists and/or antagonists for the prevention of, or treatment of infection by HCV, a flavivirus, or a pestivirus, among others.

DETAILED DESCRIPTION OF THE INVENTION

The present invention embraces the verification of a previously undefined enzymatic activity for HCV NS4B protein. Specifically, it has now been discovered that HCV NS4B protein has ATPase activity. That is, HCV NS4B protein hydrolyzes ATP to ADP. This ATPase activity of HCV NS4B is potentially essential for the life cycle of HCV. Thus, certain inhibitors and activators of HCV NS4B protein, having antiviral activity, could be used as therapeutic agents for the treatment of HCV-induced diseases in a mammal, preferably a human, infected by HCV. In particular, this treatment is of viruses linked to the Flaviviridae family, particularly HCV; flaviviruses such as yellow fever virus; Dengue virus types 1–4; and pestiviruses, such as bovine viral diarrhea virus and classic swine fever, among others, are all contemplated as being within the scope of this invention.

By identification of the novel discovery that HCV NS4B possess enzymatic activity, i.e. ATPase activity, a screening assay method may be employed to determine compounds which activate (agonists) or inhibit activation (antagonists, or otherwise called inhibitors) of the ATPase activity of this polypeptide. Thus, HCV NS4B polypeptides may be used to identify agonist or antagonists from, for example, cells, cell-free preparations, chemical compounds, combinitorial/ varimer chemical libraries, and natural product mixtures. These agonists or antagonists may be natural substrates, ligands, receptors, etc., as the case may be, of the HCV NS4B polypeptide; or may be structural or functional mimetics of this polypeptide. See Coligan, et al., *Current Protocols in Immunology* 1(2): Chapter 5 (1991). For purposes herein, enzymatic activity is the ability to hydrolyse ATP into ADP plus inorganic phosphate, or AMP plus inorganic phosphate.

In one embodiment, this invention provides for a method for identifying a compound that alters the activity of HCV NS4B protein, comprising the steps of:

(a) contacting an isolated (or extract containing NS4B protein and only ATPase activity derived from NS4B) HCV NS4B protein that is substantially free of other HCV proteins having ATPase activity with a candidate compound(s); and (b) determining whether the ATPase activity of said protein is altered by said candidate compound(s).

In another embodiment of the above screening method, this invention provides for a method for measuring the ATPase activity of HCV NS4B protein, which method comprises determining the amount of ATP metabolized to ADP and/or AMP by said protein, preferably ADP. Still another embodiment of the invention is directed to a method of screening for ATPase activity by contacting a sample containing the HCV NS4B protein with ATP and measuring the amount of ATP remaining in the sample.

In general, such screening procedures may involve using any appropriate cells which express the ATPase protein of the Flaviviridae family, particularly HCV NS4B, or which respond to this polypeptide. Such cells include, cells from mammals, yeast, insect cells, such as Drosophila or *E. coli*, preferably Drosophila cells. Cells which express the HCV NS4B polypeptide, or cell membranes containing the expressed polypeptide, or which respond to the HCV NS4B polypeptide, are then contacted with a test compound (candidate compound) to observe binding, stimulation, or inhibition of the functional response, i.e. metabolism of the ATP to ADP and/or AMP. The ability of the cells which were contacted with the candidate compound(s) are compared with the same cells which were not contacted for activity of this ATPase protein.

NS4B polypeptide, polynucleotides, and antibodies of the invention may also be used to configure assays for detecting the effect of added compounds on the production of mRNA of HCV NS4B, and protein in cells. For example, an ELISA assay may be constructed for measuring secreted or cell associated levels of the HCV NS4B protein, using monoclonal and polyclonal antibodies by standard methods known in the art. This assay can be used to discover agents which may inhibit or activate the production of the ATPase protein (also called antagonist or agonist, respectively), from suitably manipulated cells or tissues.

The HCV NS4B protein may be used to identify membrane bound or soluble receptors, if any, through standard receptor binding techniques known in the art. These include, but are not limited to, ligand binding and crosslinking assays in which the HCV NS4B protein is labeled with a radioactive isotope (e.g., $^{125}$I), chemically modified (e.g., biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of the HCV NS4B protein which compete with the binding of such a protein to its receptors. Standard methods for conducting screening assays are well understood in the art.

Examples of a potential polypeptides antagonists include antibodies or, in some cases, oligonucleotides or proteins which are closely related to the ligands, substrates, receptors, etc., as the case may be; fragment(s) of the ligands, substrates, receptors, or small molecules which bind to the HCV NS4B protein but do not elicit a response, so that the activity of the polypeptide is prevented.

Definitions

The following definitions are provided below to facilitate understanding of certain terms used frequently herein.

"HCV NS4B protein analogs" refer to polypeptides which vary from the full length protein sequence by deletion, alteration and/or addition to the amino acid sequence of the native protein. HCV NS4B protein analogs include the truncated proteins (fragments) as described below, as well as HCV NS4B muteins and fusion proteins comprising HCV NS4B protein.

"HCV NS4B protein" refers, among others, generally to a polypeptide having the amino acid sequence set forth in SEQ ID NO: 1 or an allelic variant thereof.

"HCV NS4B protein activity" or "HCV NS4B polypeptide activity" or "biological activity of the HCV NS4B or HCV NS4B polypeptide" refers to the ATPase activity of said HCV NS4B protein, but which does not possess any NS3 or other viral-related ATPase activity.

"Antibodies" as used herein includes polyclonal and monoclonal antibodies, chimeric, single chain, and humanized antibodies, as well as Fab fragments, including the products of an Fab or other immunoglobulin expression library.

"ATPase protein of the Flaviviridae family" means an enzyme capable of converting ATP to ADP, but is not limited to this enzymatic function. Moreover, this term corresponds to an enzyme phylogenetically related to viruses linked to the Flaviviridae family, such as flaviviruses, pestiviruses, HCV, and any diseases linked to HCV, among others.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein.

"Polynucleotide" generally refers to any polyribonucleotide or polydeoxribonucleotide, which may be unmodified RNA or DNA or modified RNA or DNA. This includes, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" also includes triple-stranded regions comprising RNA or DNA or both RNA and DNA; and DNAs or RNAs containing one or more modified bases and DNAs or RNAs with backbones modified for stability or for other reasons. As used herein "modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter, et al., "Analysis for protein modifications and nonprotein cofactors," *Meth. Enzymol.* (1990) 182:626–646 and Rattan, et al., "Protein Synthesis: Posttranslational Modifications and Aging," *Ann. NY Acad. Sci.* (1992) 663:48–62.

For purposes herein, the term ATPase protein and ATPase polypeptide are used interchangeably.

"Fusion protein" generally referes to a polypeptide comprising an amino acid sequence from two or more individual proteins. As used herein, it denotes a polypeptide comprising the HCV NS4B protein, truncate, mutein or a function portion thereof, fused to a non-HCV protein or polypeptide ("fusion partner"). Fusion proteins are most conveniently produced by expresion of a fused gene, which encodes a portion of one polypeptide at the 5' end and a portion of a different polypeptide at the 3' end, where the different portions are joioned in one reading frame which may be expressed in a suitable host.

"Subject" as used herein refers to a human.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, or deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER; Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J. Applied Math* (1988) 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., *SIAM J. Applied Math* (1988) 48:1073. Methods to determine identity and similarity are codified in computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Atschul, S. F. et al., *J. Molec. Biol.* (1990) 215:403).

As an illustration, by a polynucleotide having a nucleotide sequence having at least, for example, 95% "identity" to a reference nucleotide sequence encoding the polypeptide of SEQ ID NO: 1 is intended that the nucleotide sequence of the polynucleotide is identical to the reference sequence except that the polynucleotide sequence may include up to five point mutations per each 100 nucleotides of the reference polypeptide sequence of SEQ ID NO: 1. In other words, to obtain a polynucleotide having a nucleotide sequence at least 95% identical to a reference nucleotide sequence, up to 5% of the nucleotides in the reference sequence may be deleted and/or substituted with another nucleotide, and/or a number of nucleotides up to 5% of the total nucleotides in the reference sequence may be inserted into the reference sequence. These mutations of the reference sequence may occur at the 5' or 3' terminal positions of the reference nucleotide sequence, or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence of SEQ ID NO: 1 is intended that the amino acid sequence of the polypeptide is identical to the reference sequence except that the polypeptide sequence may include up to five amino acid alterations per each 100 amino acids of the reference amino acid of SEQ ID NO: 1. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

The HCV NS4B polypeptides utilized in the present invention include the polypeptide of SEQ ID NO: 1; as well as polypeptides comprising the amino acid sequence of SEQ ID NO: 1; and polypeptides comprising the amino acid sequence which have at least 60, 70, or 80% identity to that of SEQ ID NO: 1 over its entire length, and still more preferably at least 90% identity, and even still more preferably at least 95% identity to SEQ ID NO: 1. Preferably, the HCV NS4B polypeptide used herein in this invention must exhibit the desired ATPase activity.

The HCV NS4B polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production. HCV NS4B polypeptides of this form are included within the scope of this invention for use in the screening assays herein.

Another embodiment of the invention includes use of fragments of the HCV NS4B polypeptides. A fragment is a polypeptide having an amino acid sequence that entirely is the same as part, but not all, of the amino acid sequence of the aforementioned HCV NS4B polypeptide. As with HCV NS4B polypeptides, such fragments may be "free-standing," or comprised within a larger polypeptide of which they form a part or region, as a single continuous region. The invention further provides for fragments, and use thereof, of HCV NS4B protein that could include, for example, truncation polypeptides having the amino acid sequence of HCV NS4B polypeptides, except for deletion of a continuous series of residues that includes the amino terminus, or a continuous series of residues that includes the carboxyl terminus or deletion of two continuous series of residues, one including the amino terminus and one including the carboxyl terminus. Alternatively, fragments and use thereof, of the invention may be characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

The invention provides for fragments that retain biological activity, preferably ATPase enzymatic activity. Biologically active fragments are those that mediate HCV NS4B protein activity, including those with a similar activity or an improved activity, or with a decreased undesirable activity. Variants of the defined sequence and fragments also form part of the present invention. One embodiment of the invention provides for variants that vary from the referents by conservative amino acid substitutions, i.e., those that substitute a residue with another of like characteristics.

The polypeptides comprising an ATPase protein of the Flaviviridae family, particularly HCV NS4B protein, of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

TABLE 1[a]

| | | | | |
|---|---|---|---|---|
| 1712 | SQHLPYIEQ | GMMLAEQFKQ | KALGLLQTAS | RHAEVITPAV |
| 1751 | QTNWQKLEVF | WAKHMWNFIS | GIQYLAGLST | LPGNPAIASL MAFTAAVTSP |
| 1801 | LTTGQTLLFN | ILGGWVAAQL | AAPGAATAFV | GAGLAGAAIG SVGLGKVLVD |
| 1851 | ILAGYGAGVA | GALVAFKIMS | GEVPSTEDLV | NLLPAILSPG ALVVGVVSAA |
| 1901 | ILRRHVGPGE | GAVQWMNRLI | AFASRGNHVS | PTHYVPESDA AARVTAILSS |
| 1951 | LTVTQLLRRL | HQWISSECTT | PCSGSWLRDI | |

[a]An amino acid sequence of an HCV NS4B protein (SEQ ID NO: 1).

An amino acid sequence of HCV NS4B polypeptide set forth in Table 1 (SEQ ID NO: 1) was used to search the NCBI Non-redundant Protein Database using a BLASTP program. This search indicated that the NS4B polypeptide shares homology with several permeases or transport-type proteins which belong to the ATP-binding cassette (ABC) family. Closer inspection of the HCV NS4B amino acid sequence (SEQ ID NO: 1) revealed a region which had some homology to an ATP-binding site consensus sequence, as is depicted in Table 2.

TABLE 2

HCV aa# 1840–1852

```
       HCV NS4B  GSVGLGKVLVDIL
                 |  | ||     |
ATP-binding consensus  GXXGXGKXXXXXL
```

HCV NS4B protein (SEQ ID NO: 1) is contained within amino acids 1712–1972 of the HCV polyprotein. It is understood that this sequence may vary from strain to strain, as RNA viruses like HCV are known to exhibit a great deal of variation. These variations, which retain biological activity are considered within the scope of this invention.

Also contemplated within the scope of the invention are fragments, mutants, allelic variations, and analogs of HCV NS4B that possess ATPase activity. Such a fragment must include the ATP binding motif, shown above (amino acids 1840–1852), but must not possess NS3 ATPase activity. While the amino acid sequence of HCV NS4B is set forth in Table 1 (SEQ ID NO: 1), the minimum sequence necessary for ATPase activity can be determined by routine methods well known in the art. In fact, the smallest fragment of NS3 protein that still possesses ATPase activity has been determined by Kanai, et al., *FEBS Lett.* 376:221–224 (1995).

Therefore, an amino acid sequence that is larger than the NS4B protein (SEQ ID NO: 1), but still possesses ATPase activity, is contemplated within the scope of the present invention. For instance, a larger amino acid sequence of HCV NS4B protein could include amino acids 1658–1972 of the HCV polyprotein, or even into the NS3 domain, provided the fragment does not possess helicase activity of NS3.

Polynucleotides encoding an ATPase protein of the Flaviviridae family, particularly HCV NS4B protein, include isolated polynucleotides which encode the polypeptides and fragments of an ATPase protein of the Flaviviridae family, particularly HCV NS4B, and polynucleotides closely related thereto. More specifically, HCV NS4B polynucleotide of the invention include a polynucleotide comprising the nucleotide sequence encoding a HCV NS4B polypeptide of SEQ ID NO: 1. Polynucleotides of the invention further include a polynucleotide comprising a nucleotide sequence that has at least 60, 70, or 80% identity to a nucleotide sequence encoding the HCV NS4B polypeptide of SEQ ID NO: 1. In this regard, polynucleotides at least 90% identical are particularly preferred, and those with at least 95% are especially preferred. Also included under NS4B polynucleotides is a nucleotide sequence which has sufficient identity to a nucleotide sequence encoded by SEQ ID NO: 1 to hybridize under conditions useable for amplification or for use as a probe or marker. The invention also provides polynucleotides which are complementary to such polynucleotides of an ATPase protein of the Flaviviridae family, including, for example, HCV NS4B.

Cell-free translation systems can also be employed to produce ATPase proteins of the Flaviviridae family, including, for example, HCV NS4B, using RNAs derived from the DNA constructs of the present invention. For recombinant production, host cells can be genetically engineered to incorporate expression systems or portions thereof for polynucleotides of the present invention. Introduction of polynucleotides into host cells can be effected by methods described in many standard laboratory manuals, such as Davis, et al., BASIC METHODS IN MOLECULAR BIOLOGY (1986) and Sambrook, et al., MOLECULAR CLONING: A LABORATORY MANUAL, 2nd Ed., Cold Spring Harbor Laboratory Press, Cold Spring Harbor, NY (1989), such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as *streptococci, staphylococci, E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook, et al., MOLECULAR CLONING, A LABORATORY MANUAL, supra.

HCV NS4B protein has previously been expressed in baculovirus by S. E. Behrens, et al., *EMBO J*. 15:12–22 (1996) and in mammalian cells by Selby, et al., *J. Gen. Virol.* 74: 1103–1113 (1993). Moreover, the GST-fusion protein has been expressed and purified by Smith, et al., *Gene* 67: 31 (1988). Furthermore, general molecular biological techniques (cloning, expression, general art, etc.) are set forth in Ausbel, et al. (1987) *CURRENT PROTOCOLS IN MOLECULAR BIOLOGY*, supra.

For secretion of a translated protein of the invention into the lumen of the endoplasmic reticulum, into the periplasmic space or into the extracellular environment, appropriate secretion signals may be incorporated into the desired polypeptide. These signals may be endogenous to the polypeptide or they may be heterologous signals.

Cells expressing HCV NS4B protein may be harvested prior to use in the screening assay. If a polypeptide of an ATPase protein of the Flaviviridae family, particularly HCV NS4B, is secreted into the medium, the medium can be recovered in order to recover and purify the polypeptide; if produced intracellularly, the cells must first be lysed before the polypeptide is recovered. Polypeptides of an ATPase protein of the Flaviviridae family, particularly HCV NS4B, can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

It is desirable to find compounds and drugs that stimulate the ATPase function of HCV NS4B protein, on the one hand, and compounds that can inhibit the function of this polypeptide, on the other hand. In general, agonists and antagonists may potentially be employed for therapeutic and prophylactic purposes for such conditions as viruses linked to the Flaviviridae family, such as flaviviruses, pestiviruses, HCV, and any diseases linked to HCV, among others.

The ATPase activity of HCV NS4B protein was first identified by expressing the protein in insect cells (Sf9) using a baculoviral expression vector. See Example 1 below. Extracts from uninfected and HCV NS4B-baculovirus infected Sf9 cells were immunoprecipitated with HCV NS4B protein-specific antiserum and detected by Western blot. An ATPase assay was then performed with these immunoprecipitated products. See Example 2 below. Furthermore, it was discovered that deletion of the ATP-binding motif impairs the ATPase activity of HCV NS4B protein. See Example 3 below. In a preferred embodiment, this invention relates to a screening ATPasse assay for partially or fully purified HCV NS4B protein.

The assays may simply test binding of a candidate compound wherein adherence to the cells bearing the polypeptide of an ATPase protein of the Flaviviridae family, particularly HCV NS4B, and is detected by means of a label directly or indirectly associated with the candidate compound or in an assay involving competition with a labeled competitor.

Further, these assays may test whether the candidate compound results in a signal generated by activation of the polypeptide of an ATPase protein of the Flaviviridae family, particularly HCV NS4B, using detection systems appropriate to the cells bearing such a polypeptide. Inhibitors of activation are generally assayed in the presence of a known agonist, and the effect on activation by the agonist by the presence of the candidate compound is observed.

Agonists of an ATPase protein of the Flaviviridae family, particularly HCV NS4B protein, would facilitate an increase in ATPase activity, whereas antagonists of an ATPase protein of the Flaviviridae family, particularly HCV NS4B protein, would facilitate a decrease in ATPase activity. Therefore, another embodiment of the invention pertains to a screening method for agonists and antagonists of an ATPase protein of the Flaviviridae family, particularly HCV NS4B protein, wherein the activity of the ATPase protein determined would be an alteration in the level of ATPase activity resulting from contacting a candidate compound with the ATPase protein.

This invention also provides for methods of treating a human diagnosed with an active or latent infection with a virus linked to the Flaviviridae family, particularly HCV, flaviviruses such as yellow fever virus, Dengue virus types 1–4, and pestiviruses such as bovine viral diarrhea virus and classic swine fever, among others, by such candidate compounds determined by the screening assays mentioned above.

If the activity of a polypeptide of an ATPase protein of the Flaviviridae family, particularly HCV NS4B, is in excess in a human, several therapeutic approaches are available. One approach comprises administering to the subject an inhibitor compound (antagonist) as hereinabove described, along with a pharmaceutically acceptable carrier in an amount effective to inhibit the function of the ATPase protein, such as, for example, by blocking the binding of ligands, substrates, etc., or by inhibiting a second signal, and thereby alleviating the abnormal condition. In another approach, soluble forms of the ATPase protein, still capable of binding the ligand, substrate, etc. in competition with endogenous polypeptide, may be administered. Typical embodiments of such competitors comprise fragments of the ATPase protein which may be administered.

If, on the other hand, a mammal is in need of the activity of a polypeptide of an ATPase protein of the Flaviviridae family, particularly HCV NS4B, several therapeutic approaches are available. One approach comprises administering to a subject an activator compound (agonist) as hereinabove described, along with a pharmaceutically acceptable carrier in an amount effective to activate the function of the polypeptide of an ATPase protein of the Flaviviridae family, particularly HCV NS4B, such as, for example, by facilitating the binding of ligands, substrates, etc., or by activating a second signal, and thereby alleviating the abnormal condition, particularly a viral infection linked to the Flaviviridae family, particularly HCV. In another approach, soluble forms of polypeptides of an ATPase protein of the Flaviviridae family, particularly HCV NS4B, still capable of binding the ligand, substrate, etc. in competition with endogenous polypeptide may be administered. Typical embodiments of such competitors comprise fragments of the protein which may be administered.

In another approach, soluble forms of polypeptides of an ATPase protein of the Flaviviridae family, particularly HCV NS4B, still capable of binding the ligand in competition with endogenous an polypeptide of an ATPase protein of the Flaviviridae family, particularly HCV NS4B, may be administered. Typical embodiments of such competitors comprise fragments of the ATPase HCV NS4B protein.

EXAMPLES

Biological Methods

The examples below are carried out using standard techniques, which are well known and routine to those of skill in the art, except where otherwise described in detail.

Example 1

Indentification of ATPase Activity

HCV NS4B protein was expressed either in insect cells (Sf9) using baculovirus expression system or in bacteria in the form of a glutathione-S-transferase (GST) fusion protein using standard methods (Ausbel, et al. (1987) *CURRENT PROTOCOLS IN MOLECULAR BIOLOGY*, supra). Partially purified HCV NS4B protein, using either glutathione sepharose 4B (for GST-NS4B fusion protein) or immunoprecipitation with HCV NS4B-specific antiserum (for HCVNS4B protein expressed in Sf9 cells), was assayed for ATPase activity under following conditions: 50 mM Tris-HCl pH 8.0, 0.1 M NaCl, 10 mM $MgCl_2$, 1 mM DTT, 0.5 uM ATP, 10 uCi a-[$^{32}$P]-ATP(~3000 Ci/mmole), ~100 ug of protein. Reactions were carried out at 37° C. for 30 min and reaction products were analyzed by thin-layer chromatography (TLC) and autoradiography.

Example 2

ATPase Activity of HCV NS4B Expressed in Sf9 Cells Using Baculoviral Expression Vector HCV NS4B protein was expressed in Sf9 insect cells via baculovirus expression vector. Three days after cells were infected, total cellular lysates were prepared and NS4B protein production was confirmed by Western blotting analysis using rabbit antisera prepared against a NS4B-derived peptide. HCV NS4B protein was further purified using immunoprecipitation technique and protein A-Sepharose beads bound with expressed NS4B protein was subjected to ATPase assay. As a background control, cellular lysate prepared from cells infected with wild-type baculovirus (not expressing NS4B protein) was immunoprecipitated with the same anti-NS4B antisera and tested for ATPase activity.

ATPase assay was performed in the buffer containing 50 mM Tris.Cl (pH 8), 100 mM NaCl, 10 mM MgCl2, 1 mM DTT, 0.5 $\mu$M ATP, 10 $\mu$Ci $\alpha$-$^{32}$P ATP, and approximately 50 ng of NS4B protein bound with protein A-Sepharose beads. The reaction was carried at 37 C. for 45 to 60 min and 1 $\mu$l of the reaction mixture was resolved by thin layer chromatography. ATPase assay using immunoprecipitated products showed that lysate from NS4B protein expressing cells produced ATPase activity approximately 4–6 fold higher than the control lysate (from cells infected with the wild-type baculovirus).

Example 3

Deletion of the Putative ATP-Binding Motif in HCV NS4B Protein Greatly Reduces the ATPase Activity GST fusion constructs with either wild-type HCV NS4B protein (GST-NS4B) or NS4B protein with the putative ATP-binding motif deleted (GST-4BΔATP) were created. The fusion proteins were expressed in bacteria and were partially purified using glutathione-sepharose resin according to the manufacturer's recommendations (Pharmacia Biotech). The partially purified proteins were then assayed for ATPase activity as described above. Deletion of the potential ATP-binding motif significantly impaired its ATPase activity. A similar observation was also made with non-fusion NS4B proteins (wild-type and deletion mutant) expressed in insect cells using baculovirus.

All publications including, but not limited to, patents and patent applications, cited in this specification, are herein incorporated by reference as if each individual publication were specifically and individually indicated to be incorporated by reference herein as though fully set forth.

The above description fully discloses the invention, including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the examples provided herein are to be construed as merely illustrative and are not a limitation of the scope of the present invention in any way. The embodiments of the invention in which an exclusive property or privilege is claimed are defined as follows.

What is claimed is:

1. A method for measuring the ATPase activity of HCV NS4B protein, comprising the steps of:

(a) contacting a sample containing isolated HCV NS4B protein with ATP; and (b) measuring the amount of ATP remaining in the sample.

2. The method as claimed in claim 1, wherein the amount of ATP metabolized to ADP is determined.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 269 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Ser Gln His Leu Pro Tyr Ile Glu Gln Gly Met Met Leu Ala Glu Gln
 1               5                  10                  15

Phe Lys Gln Lys Ala Leu Gly Leu Leu Gln Thr Ala Ser Arg His Ala
                20                  25                  30

Glu Val Ile Thr Pro Ala Val Gln Thr Asn Trp Gln Lys Leu Glu Val
            35                  40                  45

Phe Trp Ala Lys His Met Trp Asn Phe Ile Ser Gly Ile Gln Tyr Leu
    50                  55                  60

Ala Gly Leu Ser Thr Leu Pro Gly Asn Pro Ala Ile Ala Ser Leu Met
65                  70                  75                  80

Ala Phe Thr Ala Ala Val Thr Ser Pro Leu Thr Thr Gly Gln Thr Leu
                85                  90                  95

Leu Phe Asn Ile Leu Gly Gly Trp Val Ala Ala Gln Leu Ala Ala Pro
               100                 105                 110
```

```
Gly Ala Ala Thr Ala Phe Val Gly Ala Gly Leu Ala Gly Ala Ala Ile
        115                 120                 125

Gly Ser Val Gly Leu Gly Lys Val Leu Val Asp Ile Leu Ala Gly Tyr
        130                 135                 140

Gly Ala Gly Val Ala Gly Ala Leu Val Ala Phe Lys Ile Met Ser Gly
145                 150                 155                 160

Glu Val Pro Ser Thr Glu Asp Leu Val Asn Leu Leu Pro Ala Ile Leu
                165                 170                 175

Ser Pro Gly Ala Leu Val Val Gly Val Val Ser Ala Ala Ile Leu Arg
                180                 185                 190

Arg His Val Gly Pro Gly Glu Gly Ala Val Gln Trp Met Asn Arg Leu
            195                 200                 205

Ile Ala Phe Ala Ser Arg Gly Asn His Val Ser Pro Thr His Tyr Val
        210                 215                 220

Pro Glu Ser Asp Ala Ala Ala Arg Val Thr Ala Ile Leu Ser Ser Leu
225                 230                 235                 240

Thr Val Thr Gln Leu Leu Arg Arg Leu His Gln Trp Ile Ser Ser Glu
                245                 250                 255

Cys Thr Thr Pro Cys Ser Gly Ser Trp Leu Arg Asp Ile
                260                 265
```